United States Patent
Falk

(10) Patent No.: US 7,357,029 B2
(45) Date of Patent: Apr. 15, 2008

(54) THERMAL-ACOUSTIC SCANNING SYSTEMS AND METHODS

(75) Inventor: Robert A. Falk, Bellevue, WA (US)

(73) Assignee: Optometrix, Inc., Renton, WA (US)

( * ) Notice: Subject to any disclaimer, the term of this patent is extended or adjusted under 35 U.S.C. 154(b) by 78 days.

(21) Appl. No.: 10/907,262

(22) Filed: Mar. 25, 2005

(65) Prior Publication Data

US 2005/0217381 A1  Oct. 6, 2005

Related U.S. Application Data

(60) Provisional application No. 60/558,267, filed on Mar. 31, 2004.

(51) Int. Cl.
*G01N 29/04* (2006.01)
(52) U.S. Cl. ..................... 73/643
(58) Field of Classification Search ........... 73/643, 73/601
See application file for complete search history.

(56) References Cited

U.S. PATENT DOCUMENTS

| | | | | |
|---|---|---|---|---|
| 4,046,477 A * | 9/1977 | Kaule | ...... | 73/643 |
| 4,255,971 A * | 3/1981 | Rosencwaig | ...... | 73/643 |
| 4,430,897 A * | 2/1984 | Quate | ...... | 73/643 |
| 4,484,820 A * | 11/1984 | Rosencwaig | ...... | 73/643 |
| 4,543,486 A * | 9/1985 | Rose | ...... | 73/643 |
| 7,233,284 B2 * | 6/2007 | Velicer et al. | ...... | 342/433 |

* cited by examiner

*Primary Examiner*—John E. Chapman
(74) *Attorney, Agent, or Firm*—Black Lowe & Graham PLLC

(57) ABSTRACT

Systems and methods for identifying thermal response of a test structure. An example of the system includes a device that generates a excitation beam, a scanning device that scans the thermal excitation beam over a test structure, and a detector that detects acoustic waves produced scanning by the test structure. The system also includes a display device that generates and displays an image based on the detected acoustic waves. A second detector detects a reflection of the beam off of the test structure and the display device generates and displays an image based on the detected reflection.

9 Claims, 1 Drawing Sheet

THERMAL-ACOUSTIC SCANNING SYSTEMS AND METHODS

CROSS-REFERENCE TO RELATED APPLICATIONS

This application claims the benefit of U.S. Provisional Application Ser. No. 60/558,267 filed Mar. 31, 2004, the contents of which are hereby incorporated by reference.

FIELD OF THE INVENTION

This invention relates generally to laser scanning systems and methods.

BACKGROUND OF THE INVENTION

Lasers can be used to locally heat a test structure. Localized heating produces a temperature gradient, which, in turn, produces stress and strain in the heated area. If the heating varies with time, then the resultant stress and strain will also vary with time. Time varying stress and strain produce acoustic/sound waves.

Pulsed lasers have been utilized to produce a thermal impulse response in a test structure. The resultant acoustic pulse is then detected after propagation through the test structure. These techniques are utilized to determine the acoustic propagation properties of the test structure. The acoustic propagation properties can be utilized to identify subsurface flaws and defects. These techniques are equivalent to standard ultrasound techniques utilized for the same purpose. A uniform surface structure is desirable for these techniques in order to obtain a constant amplitude and phase of the laser generated acoustic pulse.

A continuous wave (CW) laser impinging onto a test structure will produce no acoustic waves (sound). Scanning of a CW laser will produce time dependent heating. However, a uniform surface structure is still unlikely to produce any acoustic waves. It has been determined experimentally that scanning of a CW laser over a non-uniform test structure will produce acoustic waves. In particular, test structures with multiple materials present, e.g. a printed circuit board with components soldered into place, will produce a series of "pops and pings", i.e. a laser thermal-acoustic signal. These pops and pings are a result of the differential expansion and contraction causing a release of built up stress and strain of the differing materials as they are heated and cooled. In particular, components, e.g. vias, solder joints, etc., on the test structure will produce different acoustic signatures, depending on the quality of that component.

Therefore, there exists a need to identify thermal response to determine the quality of the test structure components.

BRIEF SUMMARY OF THE INVENTION

The present invention provides systems and methods for identifying thermal response of a test structure. An example of the system includes a device that generates a continuous wave (CW) thermal excitation beam, a scanning device that scans the thermal excitation beam over a test structure, and a detector that detects acoustic waves produced by the test structure. The system also includes a display device that generates and displays an image based on the detected acoustic waves.

In another aspect of the invention, a second detector detects a reflection of the beam off of the test structure and the display device generates and displays an image based on the detected reflection.

In still another aspect of the invention, the detector includes a piezoelectric detector.

BRIEF DESCRIPTION OF THE SEVERAL VIEWS OF THE DRAWING

Preferred and alternative embodiments of the present invention are described in detail below with reference to the following drawings.

DETAILED DESCRIPTION OF THE INVENTION

Figure 1:
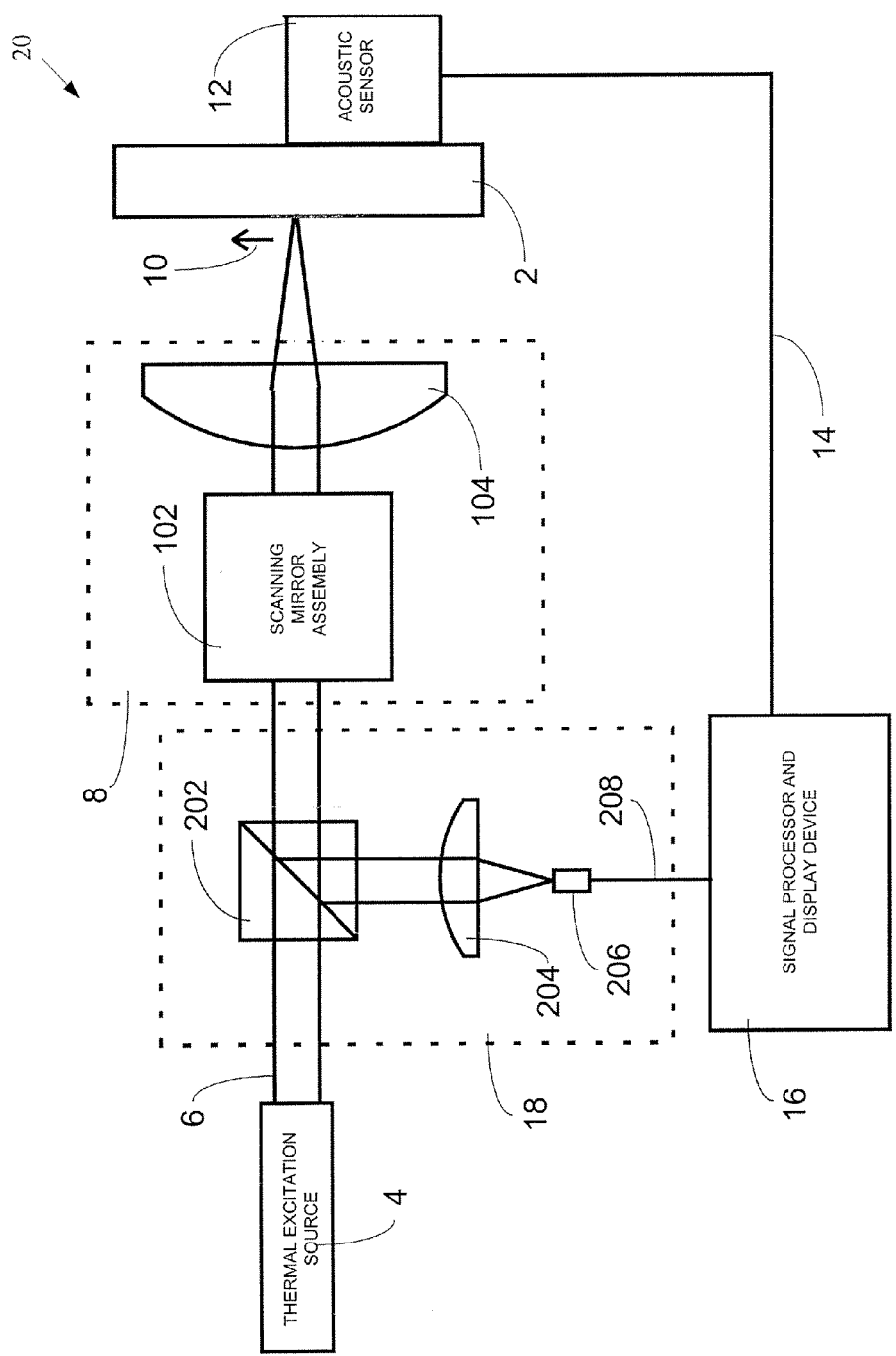
FIG. 1 is a block diagram of an example system formed in accordance with an embodiment of the present invention.

FIG. 1 a block diagram of an example system 20 is shown. The system 20 senses properties of a test structure 2. The test structure 2 can be any physical object, such as an integrated circuit, the package in which the integrated circuit is housed, a printed circuit board, composite materials, etc. In one embodiment, the system 20 locally heats the test structure 2 and then generates an image relating to the thermally induced mechanical stress/strain of the test structure 2. The stress/strain is related to the quality of the test structure 2.

The system 20 includes a thermal excitation source 4, a scanning device 8, an acoustic sensor 12, a signal processor and display device 16, and an imaging sensor 18. The thermal excitation source 4 generates a continuous wave (cw) thermal excitation beam 6. There are many options for the thermal excitation source 4, including but not limited to:

Optical, e.g. a laser
Electron beam
Ion beam
Acoustic

The thermal excitation beam 6 is directed towards the scanning device 8. If the thermal excitation beam 6 is an optical thermal excitation beam, the scanning device 8 may include a scanning mirror assembly 102 coupled with a lens 104 for focusing the excitation beam 6 onto the test structure 2. If the beam 6 is an electron or ion beam, the scanning device 8 may include equivalent electromagnetic beam deflectors and focusing elements. The scanning device 8 directs the excitation beam 6 on to the test structure 2 and scans the beam across the test structure 2. Any assembly that produces this result is acceptable. Shown in FIG. 1 is an arrow 10 that indicates a possible upwards scanning motion of the excitation beam 6. Note that the test structure 2 may also be moved to perform the scanning function (e.g., a scanning table).

The acoustic sensor 12 is placed in good acoustic contact with the test structure 2. A piezoelectric type ultrasonic transducer is an example of the acoustic sensor 12. The Piezoelectric transducer may include a fluid or gel coupling to achieve good acoustic contact. The sensor 12 may also include a laser acoustic sensor which does not require direct contact with the test structure 2. The acoustic sensor 12 picks up "pops and pings" that are produced by the test structure 2 as the beam 6 scans. The pops and pings are acoustic signals that propagate through the test structure 2 and can be picked up at any convenient point on the test structure 2. Multiple acoustic sensors 12 may be utilized to enhance the sensing process, e.g. obtain phase information. Some acoustic sensor placement points may produce better signal to noise than others. Generally an operator would select a sensor placement point that optimizes the acoustic sensing process.

The acoustic sensor 12 produces an acoustic signal, which is sent to the signal processor and display device 16. In one embodiment, the device 16 collects the output of the acoustic sensor 12 as a function of position of the thermal excitation beam 6 on the test structure 2. In another embodiment, the device 16 displays an image of the thermal-acoustic response of the test structure 2.

As a specific implementation in the form of a laser scanning imaging system, the thermal excitation source 4 is a laser. The laser beam propagates to the scanning device 8. The laser beam passes through the scanning mirror assembly 102, which deflects the laser beam at an angle versus time. The first lens 104 transforms the angular scan into a position scan on the test structure 2. In another embodiment, the first lens 104 also focuses the laser beam onto the test structure 2.

A sufficiently high power laser beam can heat the test structure 2 by tens to hundreds of degrees centigrade. This temperature rise induces stress/strain in the test structure 2 which in turn produces an acoustic response, which is picked up by the acoustic sensor 12 and displayed by the signal processor and display device 16.

An additional feature of the laser scanning implementation, is the ability to collect a reflected light image simultaneously with the thermal-acoustic image through use of the reflected light sensor 18. The thermal excitation beam 6, when in the form of a laser beam is reflected back from the test structure 2 and recollected by the first lens 104. The return beam (i.e., reflection) passes back through the scanning device 8 and redirected by a beam splitter 202 towards a second lens 204, which focuses the return beam onto a detector 206. Note that the second lens 204 is not strictly necessary in all laser-scanning configurations. The detector 206 produces a reflected light signal 208 that is proportional to the amount of the laser beam reflected back from the test structure 2. The reflected light signal 208 is sent to the signal processor and display device 16 where an image of the test structure 2 can be generated and displayed in conjunction with a thermal-acoustic image. As both images are obtained simultaneously, they will be spatially correlated. The reflected light image can therefore be used for navigation and location purposes.

Although not necessary for basic operation, the thermal excitation beam 6 could be modulated to enhance signal-to-noise via lock-in or other synchronous detection techniques.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A thermal-acoustic imaging apparatus comprising:
    a device for generating a continuous wave thermal excitation beam;
    a scanning device for scanning the thermal excitation beam over a test structure;
    a detector for detecting acoustic waves produced by scanning the test structure;
    a display device for generating an image based on the detected acoustic waves; and
    a second detector for detecting reflection of the beam off of the test structure, wherein the display device generates an image based on the detected reflection.

2. The apparatus of claim 1, wherein the device for generating thermal excitation beam includes a laser.

3. The apparatus of claim 1, wherein scanning device includes a scanning mirror assembly and a lens.

4. The apparatus in claim 1, wherein the detector for detecting acoustic waves includes a piezoelectric detector.

5. The apparatus of claim 1, wherein scanning device includes a scanning table.

6. A thermal-acoustic imaging method comprising:
    generating a continuous wave thermal excitation beam;
    scanning the thermal excitation beam over a test structure;
    detecting acoustic waves produced by the test structure;
    generating an image based on the detected acoustic waves;
    detecting reflection of the beam off of the test structure; and
    generating an image based on the detected reflection.

7. The method of claim 6, wherein the excitation beam includes a laser beam.

8. The method of claim 6, wherein scanning is performed by a scanning mirror assembly and a lens.

9. The method in claim 6, wherein detecting acoustic waves includes detecting acoustic waves using a piezoelectric detector.

* * * * *